United States Patent [19]

Yeske et al.

[11] Patent Number: 5,576,411
[45] Date of Patent: Nov. 19, 1996

[54] LOW SURFACE ENERGY POLYISOCYANATES AND THEIR USE IN ONE-OR TWO COMPONENT COATING COMPOSITIONS

[75] Inventors: Philip E. Yeske; Edward P. Squiller, both of Pittsburgh, Pa.; William E. Slack, Moundsville, W. Va.

[73] Assignee: Bayer Corporation, Pittsburgh, Pa.

[21] Appl. No.: 306,553

[22] Filed: Sep. 14, 1994

[51] Int. Cl.$^6$ .................................................. C08G 18/28
[52] U.S. Cl. ........................ 528/70; 528/49; 528/59; 528/73; 528/45; 544/193; 544/222; 252/182.15; 252/182.2
[58] Field of Search .......................... 252/182.15, 182.2; 528/70, 59, 49, 45, 73; 544/193, 222

[56] References Cited

U.S. PATENT DOCUMENTS

| | | | |
|---|---|---|---|
| 4,477,643 | 10/1984 | Keller | 528/70 |
| 4,606,737 | 8/1986 | Stern | 8/115.6 |
| 5,124,427 | 6/1992 | Potter et al. | 528/67 |
| 5,208,334 | 5/1993 | Potter et al. | 544/193 |
| 5,235,018 | 8/1993 | Potter et al. | 528/49 |
| 5,254,660 | 10/1993 | Kirchmeyer et al. | 528/49 |
| 5,283,311 | 2/1994 | Narayan et al. | 528/49 |
| 5,294,662 | 3/1994 | Moore et al. | 524/516 |

FOREIGN PATENT DOCUMENTS

| | | |
|---|---|---|
| 339862 | 11/1989 | European Pat. Off. |
| 605105 | 7/1994 | European Pat. Off. |

OTHER PUBLICATIONS

DuPont Specialty Chemicals "ZONYL"® Fluorosurfactants, Aug. 1993.

*Primary Examiner*—Rachel Johnson
*Attorney, Agent, or Firm*—Joseph C. Gil; Thomas W. Roy

[57] ABSTRACT

The present invention is directed to a polyisocyanate mixture
i) having an NCO content of 5 to 35% by weight and prepared from an organic diisocyanate,
ii) containing at least 1% by weight of isocyanurate groups (calculated as $N_3$, $C_3$, $O_3$, MW 126),
iii) containing allophanate groups in an amount such that there are more equivalents of allophanate groups than urethane groups and
iv) containing fluorine (calculated as F, AW 19) in an amount of 0.001 to 50% by weight, wherein the preceding percentages are based on the solids content of the polyisocyanate mixture, excluding any unreacted organic diisocyanate, and wherein fluorine is incorporated by reacting an isocyanate group with a compound containing two or more carbon atoms, one or more hydroxyl groups and one or more fluorine atoms to form urethane groups and converting a sufficient amount of these urethane groups to allophanate groups to satisfy the requirements of iii), provided that the polyisocyanate mixture contains sufficient allophanate groups to ensure that the polyisocyanate mixture remains stable and homogeneous in storage for 3 months at 25° C. The present invention is also directed to a process for the production this polyisocyanate mixture and to its use, optionally in blocked form, as an isocyanate component in one- or two-component coating compositions.

16 Claims, No Drawings

LOW SURFACE ENERGY POLYISOCYANATES AND THEIR USE IN ONE- OR TWO COMPONENT COATING COMPOSITIONS

BACKGROUND OF THE INVENTION

1. Field of the Invention

The present invention is directed to low surface energy polyisocyanates which contain allophanate groups, isocyanurate groups and fluorine, to a process for their preparation by a) trimerizing the isocyanate groups of organic diisocyanates in the presence of alcohols containing fluorine, and to their use in one- and two-component coating compositions.

2. Description of the Prior Art

Polyurethane coating compositions containing a polyisocyanate component, in either blocked or unblocked form and an isocyanate-reactive component, generally a high molecular weight polyol, are well known.

Although coatings prepared from these compositions possess many valuable properties, one property, in particular, which needs to be improved is the surface quality. It can be difficult to formulate coating compositions to obtain a coating having a smooth surface as opposed to one containing surface defects such as craters, etc.

It is believed that these difficulties are related to the high surface tension of the two-component coating compositions. Another problem caused by the high surface tension is the difficulty in cleaning the coatings. Regardless of their potential application area, there is a high likelihood that the coatings will be subjected to stains, graffiti, etc.

Accordingly, it is an object of the present invention to provide coating compositions which have reduced surface tension and, thus, are suitable for the production of coatings having an improved surface. It is an additional object of the present invention to provide coating compositions which have improved cleanability. It is a final object of the present invention to provide coating compositions which satisfy these requirements without substantially affecting the other valuable properties of the known polyurethane coatings.

Surprisingly, these objectives may be achieved by formulating coating compositions with the polyisocyanates according to the present invention containing allophanate groups, isocyanurate groups and fluorine which are described hereinafter.

SUMMARY OF THE INVENTION

The present invention is directed to a polyisocyanate mixture
i) having an NCO content of 5 to 35% by weight and prepared from an organic diisocyanate,
ii) containing at least 1% by weight of isocyanurate groups (calculated as $N_3C_3O_3$, MW 126),
iii) containing allophanate groups in an amount such that there are more equivalents of allophanate groups than urethane groups and
iv) containing fluorine (calculated as F, AW 19) in an amount of 0.001 to 50% by weight,
wherein the preceding percentages are based on the solids content of the polyisocyanate mixture, excluding any unreacted organic diisocyanate, and wherein fluorine is incorporated by reacting an isocyanate group with a compound containing two or more carbon atoms, one or more hydroxyl groups and one or more fluorine atoms to form urethane groups and converting a sufficient amount of these urethane groups to allophanate groups to satisfy the requirements of iii), provided that the polyisocyanate mixture contains sufficient allophanate groups to ensure that the polyisocyanate mixture remains stable and homogeneous in storage for 3 months at 25° C.

The present invention is also directed to a process for the production of a polyisocyanate mixture
i) having an NCO content of 5 to 35% by weight and prepared from an organic diisocyanate,
ii) containing at least 1% by weight of isocyanurate groups (calculated as $N_3C_3O_3$, MW 126),
iii) containing allophanate groups in an amount such that there are more equivalents of allophanate groups than urethane groups and
iv) containing fluorine (calculated as F, AW 19) in an amount of 0.001 to 50% by weight,
wherein the preceding percentages are based on the solids content of the polyisocyanate mixture, excluding any unreacted organic diisocyanate, by
a) trimerizing a portion of the isocyanate groups of an organic diisocyanate in presence of a trimerization catalyst,
b) adding 0.01 to 500 millimoles, per mole of organic diisocyanate, of a compound containing two or more carbon atoms, one or more hydroxyl groups and one or more fluorine atoms to the organic diisocyanate prior to or during step a) and optionally a non-fluorine-containing monoalcohol,
c) converting a sufficient amount of the urethane groups formed from the reaction of isocyanate groups with the compounds added in step b) to allophanate groups such that there are more equivalents of allophanate groups than urethane groups,
d) terminating the trimerization reaction at the desired degree of trimerization by adding a catalyst poison and/or by thermally deactivating the catalyst and
e) optionally removing unreacted organic diisocyanate.

The present invention also relates to the use of the polyisocyanate mixture, optionally in blocked form, as an isocyanate component in one- or two-component coating compositions.

DETAILED DESCRIPTION OF THE INVENTION

In accordance with the present invention the term "(cyclo)aliphatically bound isocyanate groups" means aliphatically and/or cycloaliphatically bound isocyanate groups. The term "monoalcohol" means a compound containing one aliphatically, cycloaliphatically, araliphatically or aromatically bound hydroxyl group.

In a preferred embodiment of the present invention the polyisocyanate mixtures are prepared from organic diisocyanates represented by the formula

wherein R represents an organic group obtained by the removing the isocyanate groups from an organic diisocyanate having aromatically or preferably (cyclo)aliphatically bound isocyanate groups and a molecular weight of 140 to 400. Preferred diisocyanates for the process according to the invention are those represented by the above formula wherein R represents a divalent aliphatic hydrocarbon group having from 4 to 18 carbon atoms, a divalent cycloaliphatic hydrocarbon group having from 5 to 15 carbon atoms, a divalent aromatic hydrocarbon group having 6 to 15 carbon atoms or a divalent araliphatic hydrocarbon group having from 7 to 15 carbon atoms.

Examples of the organic diisocyanates which are particularly suitable for the process include 1,4-tetramethylene diisocyanate, 1,6-hexamethylene diisocyanate (HDI), 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanato-methyl-3,5,5-trimethylcyclohexane (isophorone diisocyanate or IPDI), (4,4'-and/or 2,4'-diisocyanato-dicyclohexylmethane, 1,3- and 1,4-bis(isocyanato-methyl)-cyclohexane, bis-(4-isocyanato-3-methyl-cyclohexyl)-methane, xylylene diisocyanate, α,α,α',α'-tetramethyl-1,3- and/or-1,4-xylylene diisocyanate, 1-isocyanato-1-methyl-4(3)isocyanatomethyl cyclohexane, 2,4- and/or 2,6-hexahydrotoluylene diisocyanate, 2,4- and/or 2,6-toluene diisocyanate, 2,4- and/or 4,4'-diphenyl methane diisocyanate. Mixtures of these diisocyanates may also be used. Preferred diisocyanates are 1,6-hexa-methylene diisocyanate, isophorone diisocyanate and bis-(4-isocyanato-cyclohexyl)-methane; 1,6-hexamethylene diisocyanate is especially preferred.

It is also possible in accordance with the present invention to use blends of the previously mentioned diisocyanates with monoisocyanates or polyisocyanates having 3 or more isocyanate groups.

Suitable methods and catalysts for the preparation of polyisocyanates containing isocyanurate groups and allophanate groups are known and described in U.S. Pat. Nos. 5,124,427, 5,208,334 and 5,235,018, the disclosures of which are herein incorporated by reference. The trimerization of the starting diisocyanate mixture may be carried out in the absence or in the presence of Solvents which are inert to isocyanate groups. Depending on the area of application of the products according to the invention, low to medium-boiling solvents or high-boiling solvents can be used. Suitable solvents include esters such as ethyl acetate or butyl acetate; ketones such as acetone or butanone; aromatic compounds such as toluene or xylene; halogenated hydrocarbons such as methylene chloride and trichloroethylene; ethers such as diisopropyl-ether; and alkanes such as cyclohexane, petroleum ether or ligroin.

In accordance with the present invention urethane groups and preferably allophanate groups are incorporated into the polyisocyanates by the use of compounds containing two or more carbon atoms, one or more hydroxyl groups (preferably one or two hydroxyl group, more preferably one) and one or more fluorine atoms (preferably in the form of —$CF_2$— groups). Examples of these compounds include aliphatic, cycloaliphatic, araliphatic or aromatic hydroxyl group-containing compounds, which contain two or more carbon atoms and also contain fluorine atoms, preferably fluoroalkyl groups. The compounds may be linear, branched or cyclic and have a molecular weight (number average molecular weight as determined by gel permeation chromatography using polystyrene as standard) of up to 50,000, preferably up to 10,000, more preferably up to 6000 and most preferably up to 2000. These compounds generally have OH numbers of greater than 5, preferably greater than 25 and more preferably greater than 35. The hydroxyl group-containing compounds may optionally contain other hereto atoms in the form of, e.g., ether groups, ester groups, carbonate groups, acrylic groups, etc.

Thus, it is possible in accordance with the present invention to use the known polyols from polyurethane chemistry, provided that they contain fluorine, e.g. by using fluorine-containing alcohols, acids, unsaturated monomers, etc. in the preparation of these polyols. Examples of polyols, which may be prepared from fluorine-containing precursors and used in accordance with the present invention, are disclosed in U.S. Pat. No. 4,701,480, the disclosure of which is herein incorporated by reference. Additional examples of suitable fluorine-containing compounds are disclosed in U.S. Pat. Nos. 5,294,662 and 5,254,660, the disclosures of which are herein incorporated by reference.

Preferred for use according to the invention are compounds containing one or more hydroxyl groups, preferably one or two hydroxyl groups and more preferably one hydroxyl group; one or more fluoroalkyl groups; optionally one or more methylene groups; and optionally other hereto atoms such as ether groups. These compounds preferably have a molecular weight of less than 2000 or a hydroxyl number of greater than 35.

To prepare the polyisocyanates mixtures according to the invention the minimum ratio of fluorine-containing compounds to diisocyanate is about 0.01 millimoles, preferably about 0.1 millimoles and more preferably about 1 millimole of fluorine-containing compounds for each mole of diisocyanate. The maximum amount of fluorine-containing compounds to diisocyanate is about 500 millimoles, preferably about 100 millimoles and more preferably about 20 millimoles of fluorine-containing compounds for each mole of diisocyanate. The amount of the monoalcohol is selected such that the resulting polyisocyanate mixture contains a minimum of 0.001% by weight, preferably 0.01% by weight and more preferably 0.1% by weight, of fluorine (AW 19), based on solids, and a maximum of 50% by weight, preferably 10% by weight, more preferably 7% and most preferably 3% by weight of fluorine (AW 19), based on solids.

In addition to the previously described compounds containing fluorine groups, other monoalcohols and/or polyols which do not contain fluorine groups may also be used to adjust the properties of the final products. For example, monoalcohols which do not contain fluorine may be used to reduce the viscosity of the polyisocyanate mixtures. Suitable monoalcohols of this type have been disclosed in U.S. Pat. Nos. 5,124,427, 5,208,334 and 5,235,018 and 5,44,146 the disclosures of which have previously been incorporated by reference. Examples of suitable monoalcohols include methanol, ethanol, n-propanol, isopropanol, n-butanol, isobutanol and tert butanol, n-pentanol, 2-hydroxy pentane, 3-hydroxy pentane, the isomeric methyl butyl alcohols, the isomeric dimethyl propyl alcohols, neopentyl alcohol, n-hexanol, n-heptanol, n-octanol, n-nonanol, 2-ethyl hexanol, trimethyl hexanol, cyclohexanol, benzyl alcohol, phenol, the cresols, the xylenols, the trimethylphenols, decanol, dodecanol, tetradecanol, hexadecanol, octadecanol, 2,6,8-trimethylnonanol, 2-t-butyl-cyclohexanol, 4-cyclohexyl-1-butanol, 2,4,6,-trimethyl benzyl alcohol, branched chain primary alcohols and mixtures thereof (which are available from Henkel under the Standamul trademark) and mixtures of linear primary alcohols (which are available from Shell under the Neodol trademark).

Preferred ether-containing monoalcohols include ethoxy methanol, methoxy ethanol, ethoxy ethanol, the isomeric methoxy or ethoxy propanols, the isomeric propoxy methanols and ethanols, the isomeric methoxy butanols, the isomeric butoxy methanols, furfuralcohol and other monoalcohols which have a molecular weight of up to 2000 and are prepared from ethylene oxide, propylene oxide and/or butylene oxide.

It is also possible in accordance with the present invention to use mixtures of the previously described monoalcohols.

When the polyisocyanates containing isocyanurate groups and allophanate groups accordingly to the invention are prepared from monoalcohols containing ethylene oxide units, the polyisocyanates may be dispersed in water as described in U.S. Pat. No. 5,200,489, the disclosure of which is herein incorporated by reference.

The reaction temperature for isocyanurate and allophanate formation in accordance with the present invention is about 10° to 160° C., preferably about 50° to 150° C. and more preferably about 70° to 120° C.

The process according to the invention may take place either batchwise or continuously, for example, as described below. The starting diisocyanate is introduced with the exclusion of moisture and optionally with an inert gas into a suitable stirred vessel or tube and optionally mixed with a solvent which is inert to isocyanate groups such as toluene, butyl acetate, diisopropylether or cyclohexane. The previously described alcohols may be introduced into the reaction vessel in accordance with several embodiments. The alcohols may be prereacted with the starting diisocyanate to form urethane groups prior to introducing the diisocyanates into the reaction vessel; the alcohols may be mixed with the diisocyanates and introduced into the reaction vessel; the alcohols may be separately added to the reaction vessel either before or after, preferably after, the diisocyanates are added; or the catalyst may be dissolved in the alcohols prior to introducing the solution into the reaction vessel.

At a temperature of about 60° C. and in the presence of the required catalyst or catalyst solution the trimerization begins and is indicated by an exothermic reaction. As the reaction temperature increases the conversion rate of urethane groups to allophanate groups increases faster than the formation of isocyanurate groups. Accordingly, at some temperature for a given degree of trimerization, the urethane groups are substantially converted to allophanate groups, while at some lower temperature unreacted urethane groups remain. The progress of the reaction is followed by determining the NCO content by a suitable method such as titration, refractive index or IR analysis. Thus, the reaction may be terminated at the desired degree of trimerization. The termination of the trimerization reaction can take place, for example, after the NCO content has fallen by 5 to 80% by weight, preferably 10 to 60% by weight and more preferably 20 to 50% by weight, based on the initial isocyanate group content of the diisocyanate starting material.

In general, when the reaction is terminated at a high NCO content, i.e., before the NCO content has been reduced significantly, the resulting polyisocyanate mixture after removal of unreacted starting diisocyanate will have a low viscosity. To the contrary if the reaction is terminated at a low NCO content, i.e., after the NCO content has fallen significantly, then the resulting product will have a high viscosity due to the formation of polyisocyanurates and other higher molecular weight by-products of the isocyanurates and allophanates which are initially formed. This is especially true with regard to the known aliphatic diisocyanate starting materials. Cyclic diisocyanates result in extremely high viscosity products or solids after removal of unreacted monomer regardless of when the reaction is terminated.

The termination of the trimerization reaction can take place, for example, by the addition of a catalyst poison of the type named by way of example in the above-mentioned literature references. For example, when using basic catalysts the reaction is terminated by the addition of a quantity, which is at least equivalent to the catalyst quantity, of an acid chloride such as benzoyl chloride. When using heat-labile catalysts, for example, certain quaternary ammonium hydroxides, poisoning of the catalyst by the addition of a catalyst-poison may be dispensed with, since these catalysts decompose in the course of the reaction. When using such catalysts, the catalyst quantity and the reaction temperature are preferably selected such that the catalyst, which continuously decomposes, is totally decomposed when the desired degree of trimerization is reached. The quantity of catalyst or reaction temperature which is necessary to achieve this decomposition can be determined by a preliminary experiment. It is also possible initially to use a lesser quantity of a heat sensitive catalyst than is necessary to achieve the desired degree of trimerization and to subsequently catalyze the reaction by a further incremental addition of catalyst, whereby the quantity of catalyst added later is calculated such that when the desired degree of trimerization is achieved, the total quantity of catalyst is spent. The use of suspended catalysts is also possible. These catalysts are removed after achieving the desired degree of trimerization by filtering the reaction mixture.

The working-up of the reaction mixture, optionally after previous separation of insoluble catalyst constituents, may take place in various ways depending upon how the reaction was conducted and the area of application for the isocyanates. Any solvent used during trimerization reaction and any unreacted monomer present in the polyisocyanate product may be removed by distillation in known manner. The product obtained after distillation generally contains a total of less than 2, preferably less than 1% of free (unreacted) monomeric diisocyanates. The products according to the invention range from low viscosity liquids having a viscosity of 200 mPa.s to high viscosity liquids to solids.

The low viscosity products are generally obtained from aliphatic diisocyanate starting materials, such as 1,6-hexamethylene diisocyanate and have a viscosity of less than 5000, preferably less than 2000 and more preferably less than 1300 mPa.s. High viscosity products may also be obtained from these diisocyanates, but the trimerization reaction is terminated at a significantly lower NCO content. The high viscosity products have a minimum viscosity of 5000, preferably 12,000 and more preferably 15,000 to 70,000 mPa.s and a maximum viscosity of 100,000, preferably 90,000 and more preferably 70,000 mPa.s. The viscosities are determined at 100% solids at 25° C. Extremely highly viscous to solid products are generally obtained from cyclic diisocyanates such as isophorone diisocyanate, bis-(4-isocyanatocyclohexyl)-methane or the previously described aromatic diisocyanates.

The polyisocyanate mixtures obtained in accordance with the present invention have an isocyanurate group content (calculated as $N_3,C_3,O_3$, MW 126) of at least 1%, preferably at least 5% and more preferably at least 10% by weight; and an average functionality of about 2 to 7, depending upon whether a low or high viscosity product is desired. The low viscosity products prepared from aliphatic diisocyanate starting materials have an average functionality of 2 to 4, preferably 2.2 to 3.3, and an NCO content of 10 to 35%, preferably 10 to 25% and more preferably 12 to 20%. The high viscosity products prepared from aliphatic diisocyanate starting materials have an average functionality of 3 to 7, preferably 3.5 to 6; an NCO content of 5 to 25%, preferably 10 to 17% and an equivalent weight which is at least 30% greater, preferably 40% greater and more preferably 50% greater, than the molecular weight of the monomeric isocyanate used to prepare the polyisocyanate mixture. The extremely highly viscous to solid products prepared from cyclic diisocyanate starting materials have an average functionality of 2 to 6 preferably 2.2 to 5, and NCO content of 10 to 40%, preferably 12 to 25% by weight.

The polyisocyanate mixtures according to the invention, which are prepared from aliphatic, cycloaliphatic or araliphatic diisocyanate starting materials, especially the low viscosity products prepared from aliphatic diisocyanate starting materials, may be almost colorless, i.e., they have a yellowness index as measured on the APHA color scale of 10 to 200, preferably 30 to 150 and more preferably 50 to 100.

In the low viscosity products prepared from aliphatic diisocyanate starting materials, the ratio of monoisocyanurate groups to mono-allophanate groups in the polyisocyanates according to the invention is about 10:1 to 1:10, preferably about 5:1 to 1:7. These values may be determined by gel permeation chromatography (GPC) by determining the areas under the peaks for the monoisocyanurate and monoallophanate groups. In accordance with the present invention the term "monoisocyanurate" means a polyisocyanate containing one isocyanurate group and formed from three diisocyanate molecules, and the term "polyiso-cyanurate" means a polyisocyanate containing more than one isocyanurate group. The term "monoallophanate" means a polyisocyanate containing one allophanate group and formed from two diisocyanate molecules and 1 monoalcohol molecule, and the term "polyallophanate" means a polyisocyanate containing more than one allophanate group.

The products according to the present invention are polyisocyanates containing isocyanurate groups, allophanate groups and fluorine, preferably in the form of fluoroalkyl groups ($-CF_2-$). The products may also contain residual urethane groups which are not converted to allophanate groups depending upon the temperature maintained during the reaction and the degree of isocyanate group consumption. While it is preferred to convert at least 50%, preferably at least 70% and more preferably at least 90% of the urethane groups formed from the fluorine-containing hydroxyl compounds to allophanate groups, it is not necessary provided that the number of equivalents of allophanate groups exceeds the number of equivalents of urethane groups and provided that the polyisocyanate mixture contains sufficient allophanate groups to ensure that the polyisocyanate mixture remains stable and homogeneous in storage for 3 months at 25° C. If the polyisocyanate mixture contains an insufficient number of allophanate groups, the mixture may be cloudy and a gradual settling of insoluble constituents may take place during storage. For example, it might not be necessary to convert the urethane groups formed from the fluorine-containing hydroxyl compounds to allophanate groups when the polyisocyanate mixture contains allophanate groups formed from non-fluorine-containing monoalcohols as previously discussed.

The products according to the invention are valuable starting materials for the production of polyisocyanate polyaddition products by reaction with compounds containing at least two isocyanate reactive groups. The products according to the invention may also be moisture-cured to form coatings. Preferred products are one or two-component coating compositions, more preferably polyurethane coating compositions. When the polyisocyanates are unblocked, two-component compositions are obtained. To the contrary when the polyisocyanates are blocked, one-component compositions are obtained.

Prior to their use in coating compositions, the polyisocyanate mixtures according to the invention may be blended with other known polyisocyanates, e.g., polyisocyanate adducts containing biuret, isocyanurate, allophanate, urethane, urea, carbodiimide, and/or uretdione groups. The amount of the polyisocyanates mixtures according to the invention that must be blended with these other polyisocyanates is dependent upon the fluorine content of the polyisocyanates according to the invention, the intended application of the resulting coating compositions and the amount of low surface energy properties which are desired for this application.

To obtain low surface energy properties the resulting polyisocyanate blends should contain a minimum of 0.001% by weight, preferably 0.01% by weight and more preferably 0.1% by weight, of fluorine (AW 19), based on solids, and a maximum of 10% by weight, preferably 7% by weight and more preferably 3% by weight of fluorine (AW 19), based on solids. By knowing the fluorine content of the polyisocyanate mixtures according to the invention and the desired fluorine content of the resulting polyisocyanate blends, the relative amounts of the polyisocyanate mixtures and the other polyisocyanates may be readily determined.

In accordance with the present invention any of the polyisocyanate mixtures according to the invention can be blended with other polyisocyanates. However, preferably the polyisocyanate mixtures to be blended have a minimum fluorine content of 5% by weight, preferably 10% by weight and more preferably 20% by weight, and a maximum fluorine content of 50% by weight, preferably 45% by weight. These socalled "concentrates" may then be blended with other polyisocyanates to form polyisocyanate blends that may be used to prepare coatings having low surface energy characteristics.

Preferred reaction partners for the products according to the invention are the polyhydroxy polyesters, polyhydroxy polyethers, polyhydroxy polyacrylates, polyhydroxy polylactones, polyhydroxy polyurethanes, polyhydroxy polyepoxides and optionally low molecular weight, polyhydric alcohols known from polyurethane coatings technology. Polyamines, particularly in blocked form, for example as polyketimines, oxazolidines or polyaldimines are also suitable reaction partners for the products according to the invention. Also suitable are polyaspartic acid derivatives (succinates) containing secondary amino groups, which also function as reactive diluents.

To prepare the coating compositions the amount of the polyisocyanate component and the isocyanate reactive component are selected to provide equivalent ratios of isocyanate groups (whether present in blocked or unblocked form) to isocyanate-reactive groups of about 0.8 to 3, preferably about 0.9 to 1.5.

To accelerate hardening, the coating compositions may contain known polyurethane catalysts, e.g., tertiary amines such as triethylamine, pyridine, methyl pyridine, benzyl dimethylamine, N,N-dimethylamino cyclohexane, N-methyl-piperidine, pentamethyl diethylene triamine, 1,4-diazabicyclo[2,2,2]-octane and N,N'-dimethyl piperazine; or metal salts such as iron(III)-chloride, zinc chloride, zinc-2-ethyl caproate, tin(II)-ethyl caproate, dibutyltin(IV)-dilaurate and molybdenum glycolate.

The products according to the invention are also valuable starting materials for one-component coating compositions, preferably poly-urethane coating compositions, in which the isocyanate groups are used in a form blocked by known blocking agents. The blocking reaction is carried out in known manner by reacting the isocyanate groups with suitable blocking agents, preferably at an elevated temperature (e.g. about 40° to 160° C.), and optionally in the presence of a suitable catalyst, for example, the previously described tertiary amines or metal salts.

Suitable blocking agents include monophenols such as phenol, the cresols, the trimethylphenols and the tert.butyl phenols; tertiary alcohols such as tert.butanol, tert.amyl alcohol and dimethylphenyl carbinol; compounds which easily form enols such as acetoacetic ester, acetyl acetone and malonic acid derivatives, e.g. malonic acid diethylester; secondary aromatic amines such as N-methyl aniline, the N-methyl toluidine, N-phenyl toluidine and N-phenyl xylidine; imides such as succinimide; lactams such as ε-caprolactam and δ-valerolactam; pyrazoles such as 3,5-dimethyl pyrazole; oximes such as butanone oxime, methyl amyl ketoxime and cyclohexanone oxime; mercaptans such as methyl mercaptan, ethyl mercaptan, butyl mercaptan, 2-mercaptobenzthiazole, α-naphthyl mercaptan and dodecyl mercaptan; and triazoles such as 1H-1,2,4-triazole.

The polyisocyanate mixtures according to the invention may also be used as the polyisocyanate component in two-component water borne coating compositions. To be useful for in these compositions the polyisocyanate mixtures must be rendered hydrophilic either by blending with external emulsifiers or by a reaction with compounds containing cationic, anionic or non-ionic groups. Methods for rendering the polyisocyanates hydrophilic are disclosed in copending application, U.S. Pat. Nos. 5,194,487 and 5,200,489, the disclosures of which are herein incorporated by reference. The reduced surface tension of the modified polyisocyanate mixtures enhance pigment dispersion and substrate wetting.

The coating compositions may also contain other additives such as pigments, dyes, fillers, levelling agents and solvents. The coating compositions may be applied to the substrate to be coated in solution or from the melt by conventional methods such as painting, rolling, pouring or spraying.

The coating compositions containing the polyisocyanates according to the invention provide coatings which have good dry times, adhere surprisingly well to a metallic base, and are particularly light-fast, color-stable in the presence of heat and very resistant to abrasion. Furthermore, they are characterized by high hardness, elasticity, very good resistance to chemicals, high gloss, good weather resistance, good environmental etch resistance and good pigmenting qualities. Above all, the coating compositions have an excellent surface appearance and excellent cleanability.

The invention is further illustrated, but is not intended to be limited by the following examples in which all parts and percentages are by weight unless otherwise specified.

EXAMPLES

Alcohol 1
A perfluorinated polypropylene oxide, EO-capped monoalcohol, MW 757 (available from Ausimont as Galden-TX).

Alcohol 2
A perfluorinated monoalcohol, MW 443 (available from DuPont as Zonyl BA-L).

Alcohol 3
2,3,4,5,6-Pentafluorobenzyl monoalcohol (available from Aldrich).

Alcohol 4
A perfluorinated polyether, EO-capped dialcohol, MW 2100 (available from Ausimont as Fluorolink E).

Examples 1–13

Polyisocyanates Containing Allophanate and Isocyanurate Groups Prepared From HDI or IPDI and a Fluorinated Alcohol To a 3-neck flask equipped with a gas bubbler, mechanical stirrer, thermometer and condenser were added 100 parts of a diisocyanate monomer and an amount of fluorinated alcohol, as set forth in Table 1. Dry nitrogen was bubbled through the stirred reaction mixture while it was heated at 80° C. When the urethane reaction was complete (about 1 hour), the temperature was raised to 90° C. To the reaction mixture at 90° C. was added an amount of a 5% solution of trimethylbenzylammonium hydroxide dissolved in 1-butanol as set forth in Table 1 over a 90 minute period. When the NCO content reached the value set forth in Table 1, the reaction was stopped by adding 1.1 equivalents (based on catalyst solution) of a 25% solution of di(2-ethylhexyl)phosphate dissolved in HDI. The excess monomer was removed by thin film evaporation to provide a polyisocyanate having the properties set forth in Table 1.

Comparison Example 1

Polyisocyanate Containing Isocyanurate Groups and Prepared From HDI

An isocyanurate group-containing polyisocyanate prepared from 1,6-hexamethylene diisocyanate and having an isocyanate content of 21.6%, a content of monomeric diisocyanate of <0.2% and a viscosity at 20° C. of 3000 mPa.s (available from Miles Inc. as Desmodur N 3300). This polyisocyanate corresponds to those prepared in Examples 1–13 with the exception that a fluorine-containing monoalcohol was not used in the production of the polyisocyanate.

It is apparent from the data set forth in Table 1, that the presence of fluorine is necessary to obtain low surface energies.

TABLE 1

| Example # | Monomer | Modifying ROH | pbw/100 g HDI | ppm Catalyst | Crude % NCO | Resin Viscosity (mPa · s) | Resin Surface Energy (Dynes/cm) | Resin Appearance |
|---|---|---|---|---|---|---|---|---|
| Comp. 1 | HDI | None | • | | | 3000 | 48.6 | Clear |
| 1 | HDI | Alcohol 1 | 4.00 | 120 | 33.7 | 8350 | 21.3 | Clear |
| 2 | HDI | Alcohol 1 | 2.00 | 163 | 39.1 | 1840 | 21.1 | Clear |
| 3 | HDI | Alcohol 1 | 1.00 | 165 | 39.1 | 2000 | 20.6 | Clear |
| 4 | HDI | Alcohol 1 | 0.60 | 63 | 40.0 | 2160 | 20.2 | Clear |
| 5 | HDI | Alcohol 1 | 0.06 | 48 | 40.1 | 2288 | 30.8 | Clear |
| 6 | HDI | Alcohol 1 | 0.01 | 100 | 39.5 | 5000 | 41.4 | Clear |
| 7 | HDI | Alcohol 2 | 2.00 | 286 | 39.5 | 1300 | 27 | Clear |
| 8 | HDI | Alcohol 2 | 0.20 | 299 | 40.4 | 1820 | 37 | Clear |
| 9 | HDI | Alcohol 2 | 0.01 | 125 | 40.4 | 4400 | 42.1 | Clear |

TABLE 1-continued

| Example # | Monomer | Modifying ROH | pbw/100 g HDI | ppm Catalyst | Crude % NCO | Resin Viscosity (mPa · s) | Resin Surface Energy (Dynes/cm) | Resin Appearance |
|---|---|---|---|---|---|---|---|---|
| 10 | HDI | Alcohol 1 | 1.20 | 88 | 26.4 | 51,800 | • | Clear |
| 11 | HDI | Alcohol 3 | 1.00 | 89 | 40.1 | 2089 | 40.9 | Clear |
| 12 | HDI | Alcohol 4 | 0.60 | 89 | 43.0 | 1130 | 24.5 | Clear |
| 13 | IPDI | Alcohol 1 | 1.00 | 49 | 31.1 | 375 • 70% solids | 25.8 | Clear |

Examples 14–15

Polyisocyanates Containing Allophanate Groups and Isocyanurate Groups Prepared From HDI, a Fluorinated Monoalcohol and 1-Butanol To a 3-neck flask equipped with a gas bubbler, mechanical stirrer, thermometer and condenser were added 100 pads of hexamethylene diisocyanate, 4.4 pads 1-butanol and an amount of a fluorinated monoalcohol, as set forth in Table 2.

Dry nitrogen was bubbled through the stirred reaction mixture while it was heated at 80° C. When the urethane reaction was complete (about 1 hour), the temperature was raised to 90° C. To the reaction mixture at 90° C. was added an amount of a 5% solution of trimethylbenzylammonium hydroxide dissolved in 1-butanol as set forth in Table 2 over a 90 minute period. When the NCO content reached the value set forth in Table 2, the reaction was stopped by adding 1.1 equivalents (based on catalyst solution) of a 25% solution of di(2-ethylhexyl)phosphate dissolved in HDI. The excess monomer was removed by thin film evaporation to provide a polyisocyanate having the properties set forth in Table 2.

Comparison Example 2

Polyisocyanates Containing Allophanate and Isocyanurate Groups Prepared From HDI or IPDI and a Non-Fluorinated Alcohol A polyisocyanate containing isocyanurate groups and allophanate groups was prepared by adding 301.7 pads of hexamethylene diisocyanate and 13.3 pads of 1-butanol to a 500 ml 3-neck flask equipped with a gas bubbler, mechanical stirrer, thermometer and condenser. The stirred mixture was heated for 1 hour at 60° C. while dry nitrogen was bubbled through the reaction mixture. The temperature of the reaction mixture was then raised to 90° C. To the reaction mixture at 90° C. were added 0.214 pads of a 4.4% solution of N,N,N-trimethyl-N-benzyl-ammonium hydroxide in 1-butanol. When the reaction mixture reached an NCO content of 34.8%, the reaction was stopped by adding 0.214 parts of di-(2-ethylhexyl)-phosphate. The excess monomer was removed by thin film evaporation to provide an almost colorless, clear liquid having a viscosity of 630 mPa.s (25° C.), an NCO content of 19.7% and a free monomer (HDI) content of 0.35%. The yield was 48.6%. This polyisocyanate corresponds to those of Examples 1–13 with the exception that the monoalcohol did not contain fluorine.

It is apparent from the data set forth in Table 2 that the presence of allophanate groups alone do not result in polyisocyanates having low surface energies.

TABLE 2

| Example # | Monomer | Modifying ROH | pbw/100 g HDI | ppm catalyst | Crude % NCO | Resin Viscosity (mPa · s) | Resin Surface Energy (Dynes/cm) | Resin Appearance |
|---|---|---|---|---|---|---|---|---|
| Comp. 2 | HDI | Butanol | 4.40 | | | 800 | 43.3 | Clear |
| 14 | HDI | Butanol/Alcohol 1 | 4.4/0.1 | 150 | 36.3 | 450 | 27.1 | Clear |
| 15 | HDI | Butanol/Alcohol 1 | 4.4/1.0 | 119 | 35.4 | 320 | 31.7 | Clear |

Comparison Examples 3–4

Polyisocyanates Containing Urethane Groups

To a 1L, 3-neck flask equipped with a gas bubbler, mechanical stirrer, thermometer and condenser were added 98 parts of the polyisocyanate described in Comparison Example 1 and 2 parts of the fluorinated monoalcohol set forth in Table 3. Dry nitrogen was bubbled through the stirred reaction mixture while it was heated at 50° C. for 9 hours. The resulting polyisocyanate had the properties set forth in Table 3. Over a 1 week period, both of the polyisocyanates from these comparison examples completely separated into two phases.

Example 16–17

Polyisocyanates Containing Urethane Groups

To a 1L, 3-neck flask equipped with a gas bubbler, mechanical stirrer, thermometer and condenser were added 98 parts of the polyisocyanate prepared in Comparison Example 2 and the amount of the fluorinated monoalcohol set forth in Table 3. Dry nitrogen was bubbled through the stirred reaction mixture while it was heated at 50° C. for 9 hours. The resulting polyisocyanate had the properties set forth in Table 3.

The only difference between Comparison Examples 3 and 4 and Examples 16 and 17 is that the polyisocyanate used as the starting material in the comparison examples (i.e., the polyisocyanate from Comp. Ex. 1) did not contain allophanate groups, while the polyisocyanate used as the starting material in the examples according to the invention (i.e., the polyisocyanate from Comp. Ex. 2) did contain allophanate groups. These examples demonstrate that allophanate groups must be present to obtain polyisocyanates having low surface energies, but that fluorine does not need to be incorporated through the allophanate groups.

All reported solid (coating) surface energies (in dynes/cm) were obtained by the Owens-Wendt procedure. The contact angle of two solvents (water and methylene iodide) were measured with a goniometer. Several readings were

TABLE 3

| Example # | Monomer | Modifying ROH | pbw/100 g HDI | ppm/catalyst | Crude % NCO | Resin Viscosity (mPa · s) | Resin Surface Energy (Dynes/cm) | Resin Appearance |
| --- | --- | --- | --- | --- | --- | --- | --- | --- |
| Comp. 1 | HDI | None | • | | | 3000 | 48.6 | Clear |
| Comp. 3 | HDI | Alcohol 2 | 2.00 | • | • | 3400 | 29.8 | Cloudy, 2-phase |
| Comp. 4 | HDI | Alcohol 1 | 2.00 | • | • | 3600 | 22.5 | Cloudy, 2-phase |
| Comp. 2 | HDI | Butanol | 4.40 | | | 800 | 43.3 | Clear |
| 16 | HDI | Alcohol 1 | 0.10 | • | • | 1640 | 30.3 | Clear |
| 17 | HDI | Alcohol 1 | 1.00 | • | • | 1550 | 18.3 | Clear |

Coatings Prepared From Examples 1–13 and Comparison Examples 1–4

Coating compositions containing a hydroxyl-functional polyacrylate present as 70% solution in n-butyl acetate and having an average solution equivalent weight of 607 (Desmophen A LS-2945, available from Miles) and the polyisocyanates set forth in Table 4 were prepared such that the NCO:OH equivalent ratio was 1.1:1. The coating compositions were reduced to 70% solids with Exxate 700 solvent, n-butyl acetate and methyl amyl ketone (1:4:1) and allowed to react for five minutes. At that time, coatings having a 5 mil wet film thickness were drawndown onto cold rolled steel and onto glass and allowed to cure for two weeks at 70° F. and 55% relative humidity. The appearance and properties of the coatings are set forth out in Table 4.

Table 4 demonstrates that polyisocyanates that have low surface energies can be used to produce coatings that have low surface energies. To the contrary Table 4 also demonstrates that polyisocyanates that have high surface energies cannot be used to produce coatings that have low surface energies.

taken and averaged. The averages were then used to calculate the solid surface energy of the coating, taking into account the contributions of polar and dispersive forces.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polyisocyanate mixture
   i) having an NCO content of 5 to 35% by weight and prepared from an organic diisocyanate,
   ii) containing at least 5% by weight of isocyanurate groups (calculated as $N_3,C_3,O_3$, MW 126),
   iii) containing allophanate groups in an amount such that there are more equivalents of allophanate groups than urethane groups and
   iv) containing fluorine (calculated as F, AW 19) in an amount of 0.001 to 50% by weight,

TABLE 4

| Example # | Modifying ROH | Film Surface Energy (Dynes/cm) | Film Appearance | MEK DR | Pendulum Hardness (sec) |
| --- | --- | --- | --- | --- | --- |
| Comp. 1 | None | 43.7 | Clear | >200 | 182.0 |
| Comp. 2 | Butanol | 43.6 | Clear | >200 | 137.2 |
| 1 | Alcohol 1 | 28.1 | Clear | >200 | 170.8 |
| 2 | Alcohol 1 | 26.2 | Clear | >200 | 176.4 |
| 3 | Alcohol 1 | 26.1 | Clear | >200 | 165.2 |
| 7 | Alcohol 2 | 19.4 | Clear | >200 | 184.8 |
| 8 | Alcohol 2 | 33.1 | Clear | >200 | 149.8 |
| 10 | Alcohol 1 | 21.6 | Clear | >200 | 207.2 |
| 11 | Alcohol 3 | 39.6 | Clear | >200 | 189.0 |
| 12 | Alcohol 4 | 21.9 | Clear | >200 | 194.6 |
| 13 | Alcohol 1 | 36.6 | Clear | >200 | 194.6 |
| Comp. 3 | Alcohol 2 | 20.4 | Hazy | >200 | 191.8 |
| Comp. 4 | Alcohol 1 | 20.8 | Hazy | >200 | 187.6 |

Surface Energy Measurements (see attached tables)

All reported liquid (resin) surface energies (in dynes/cm) were obtained using the ring or Du Noüy method. In this static method, the force applied on a thin platinum ring was measured using a tensiometer.

wherein the preceding percentages are based on the solids content of the polyisocyanate mixture, excluding any unreacted organic diisocyanate, and wherein fluorine is incorporated by reacting an isocyanate group with a compound containing two or more carbon atoms, one or more hydroxyl groups and one or more fluorine atoms to form urethane groups and converting a sufficient amount of said urethane groups to allophanate groups to satisfy the requirements of iii), provided that the polyisocyanate mixture contains sufficient allophanate groups to ensure that the polyisocyanate mixture remains stable and homogeneous in storage for 3 months at 25° C.

2. The polyisocyanate mixture of claim 1 wherein said organic diisocyanate comprises 1,6-hexamethylene diisocyanate.

3. The polyisocyanate mixture of claim 1 which contains less than 10% by weight, based on solids, of fluorine.

4. The polyisocyanate mixture of claim 2 which contains less than 10% by weight, based on solids, of fluorine.

5. The polyisocyanate mixture of claim 3 which has a viscosity of less than 5000 mPa.s at 25° C. and contains monoisocyanurate groups and monoallophanate groups in an equivalent ratio of 10:1 to 1:10.

6. The polyisocyanate mixture of claim 4 which has a viscosity of less than 5000 mPa.s at 25° C. and contains monoisocyanurate groups and monoallophanate groups in an equivalent ratio of 10:1 to 1:10.

7. The polyisocyanate mixture of claim 1 which has a fluorine content of 20 to 50% by weight.

8. A polyisocyanate mixture
   i) having an NCO content of 5 to 35% by weight, based on solids, and prepared from an organic diisocyanate,
   ii) containing at least 5% by weight, based on solids, of isocyanurate groups (calculated as $N_3,C_3,O_3$, MW 126),
   iii) containing allophanate groups in an amount such that there are more equivalents of allophanate groups than urethane groups and
   iv) containing fluorine (calculated as F, AW 19) in an amount of 0.001 to 50% by weight, based on solids,
wherein fluorine is incorporated by reacting an isocyanate group with a compound containing two or more carbon atoms, one hydroxyl group and two or more fluorine atoms in the form of —$CF_2$— groups to form urethane groups and converting at least 70% of said urethane groups to allophanate groups to satisfy the requirements of iii).

9. The polyisocyanate mixture of claim 8 wherein said organic diisocyanate comprises 1,6-hexamethylene diisocyanate.

10. The polyisocyanate mixture of claim 8 which contains less than 10% by weight, based on solids, of fluorine.

11. The polyisocyanate mixture of claim 9 which contains less than 10% by weight, based on solids, of fluorine.

12. The polyisocyanate mixture of claim 10 which has a viscosity of less than 5000 mPa.s at 25° C. and contains monoisocyanurate groups and monoallophanate groups in an equivalent ratio of 10:1 to 1:10.

13. The polyisocyanate mixture of claim 11 which has a viscosity of less than 5000 mPa.s at 25° C. and contains monoisocyanurate groups and monoallophanate groups in an equivalent ratio of 10:1 to 1:10.

14. The polyisocyanate mixture of claim 8 which has a fluorine content of 20 to 50% by weight.

15. A process for the production of a polyisocyanate mixture
   i) having an NCO content of 5 to 35% by weight and prepared from an organic diisocyanate,
   ii) containing at least 5% by weight of isocyanurate groups (calculated as $N_3,C_3,O_3$, MW 126),
   iii) containing allophanate groups in an amount such that there are more equivalents of allophanate groups than urethane groups and
   iv) containing fluorine (calculated as F, AW 19) in an amount of 0.001 to 50% by weight,
wherein the preceding percentages are based on the solids content of the polyisocyanate mixture, excluding any unreacted organic diisocyanate, which comprises
   a) trimerizing a portion of the isocyanate groups of an organic diisocyanate in presence of a trimerization catalyst,
   b) adding 0.01 to 500 millimoles, per mole of organic diisocyanate, of a compound containing two or more carbon atoms, one or more hydroxyl groups and one or more fluorine atoms to the organic diisocyanate prior to or during step a) and optionally a non-fluorine-containing monoalcohol,
   c) converting a sufficient amount of the urethane groups formed from the reaction of isocyanate groups with the compounds added in step b) to allophanate groups such that there are more equivalents of allophanate groups than urethane groups,
   d) terminating the trimerization reaction at the desired degree of trimerization by adding a catalyst poison and/or by thermally deactivating the catalyst and
   e) optionally removing unreacted organic diisocyanate.

16. A one- or two-component coating composition containing the polyisocyanate mixture of claim 1, optionally blocked by blocking agents for isocyanate groups, and a compound containing isocyanate-reactive groups.

* * * * *